United States Patent
Rauhala et al.

(10) Patent No.: US 11,688,520 B2
(45) Date of Patent: Jun. 27, 2023

(54) SYSTEM AND METHOD FOR ESTIMATING CALORIE BURN FOR WORKOUTS

(71) Applicant: PEAR Sports LLC, Newport Beach, CA (US)

(72) Inventors: Kari Kristian Rauhala, Solana Beach, CA (US); Eric Franchomme, San Diego, CA (US); Micah Kendrick Peng, San Diego, CA (US); Sam Daniel Arvidsson, San Diego, CA (US); Anton Dembowski, Los Angeles, CA (US); Gregory John Altin, San Diego, CA (US)

(73) Assignee: PEAR Sports LLC, Newport Beach, CA (US)

( * ) Notice: Subject to any disclaimer, the term of this patent is extended or adjusted under 35 U.S.C. 154(b) by 913 days.

(21) Appl. No.: 16/459,488

(22) Filed: Jul. 1, 2019

(65) Prior Publication Data

US 2020/0001133 A1    Jan. 2, 2020

Related U.S. Application Data

(60) Provisional application No. 62/692,506, filed on Jun. 29, 2018.

(51) Int. Cl.
| | |
|---|---|
| *G16H 50/30* | (2018.01) |
| *G16H 20/30* | (2018.01) |
| *G16H 10/60* | (2018.01) |
| *A63B 24/00* | (2006.01) |
| *A61B 5/00* | (2006.01) |

(52) U.S. Cl.
CPC ........... *G16H 50/30* (2018.01); *A61B 5/4866* (2013.01); *A63B 24/0062* (2013.01); *A63B 24/0075* (2013.01); *G16H 10/60* (2018.01); *G16H 20/30* (2018.01); *A61B 5/0002* (2013.01); *A61B 2503/10* (2013.01)

(58) Field of Classification Search
CPC ........ G16H 50/30; G16H 10/60; G16H 20/30; A61B 5/4866; A61B 5/0002; A61B 2503/10; A61B 5/1118; A63B 24/0062; A63B 24/0075
See application file for complete search history.

(56) References Cited

U.S. PATENT DOCUMENTS

| | | | | |
|---|---|---|---|---|
| 2016/0058337 | A1* | 3/2016 | Blahnik | G16H 20/40 600/595 |
| 2016/0101319 | A1* | 4/2016 | Tanabe | A61B 5/1118 434/255 |

\* cited by examiner

*Primary Examiner* — Jeffrey S Vanderveen
(74) *Attorney, Agent, or Firm* — Lowenstein Sandler LLP

(57) ABSTRACT

A system and method for estimating a caloric expenditure by a user for a workout. A system includes one or more wearable sensors configured to be worn by the user, each sensing biometric data and/or performance data about the user during the workout. A mobile computing device includes a memory that stores a user profile for the user and a metabolic equivalent of tasks (METs) table, and one or more communication inputs for receiving the biometric data from the one or more wearable sensors. A computer processor associated with the mobile computing device is configured by an application to calculate the caloric expenditure by the user for the workout according to one or more fields of the METs table and the user profile, and based on the workout defined by the application.

12 Claims, 3 Drawing Sheets

SYSTEM AND METHOD FOR ESTIMATING CALORIE BURN FOR WORKOUTS

CROSS-REFERENCE TO RELATED APPLICATION

This application claims the benefit of U.S. Provisional application No. 62/692,506, filed Jun. 29, 2018, which is hereby incorporated herein by reference in its entirety.

TECHNICAL FIELD

The subject matter described herein relates to methods and devices for tracking activity and improving a workout by a user, and more particularly to a system and method for estimating calorie burn for workouts.

BACKGROUND

In the fields of health and fitness, there exists a problem in estimating calorie "burn" per specific workout without a heart rate monitor (HRM), which can be integrated with any number of wearable tracking devices. A calorie is a unit of energy, and defines an amount of energy needed to increase the temperature of 1 gram of water by 1° C. For a workout, a calorie is conventionally used to defined a unit of energy that is expended to accomplish some physical activity. The longer and/or more intense the activity, the more calories are expended or "burned," to use industry parlance.

It is known that by using a HRM, a calorie burn for a user can be estimated very accurately. However, not everyone uses or wears an HRM. It is known that The Compendium of Physical Activities keeps a comprehensive list of metabolic equivalent of tasks (METs), where such tasks can relate to specific workouts. The MET value is used to estimate calories burned in the activity. Calories=MET_factor×time (h)×weight (kg). However, this list is very long and has hundreds of activities with an estimated MET value. It is very hard to find the correct MET value from the list.

Accordingly, what is needed is a system and method for estimating calorie burn for workouts generated for a user by a computer-implemented physical activity coaching platform that includes a workout builder application.

SUMMARY

This document describes a system and method for estimating calorie burn for workouts generated for a user by a computer-implemented physical activity coaching platform that includes a workout builder application. In some aspects, the system and method employs data mining techniques for estimating METs for specific workouts, based on user profiles, workout activities, and environmental factors, to name a just a few.

In one aspect, a system includes a mobile computing device having a memory that stores a user profile for the user, a workout performance history for the user and/or other users, and a metabolic equivalent of tasks (METs) table, the mobile computing device further having one or more communication inputs for receiving the biometric data and/or performance data about the user during the workout. The system further includes a computer processor associated with the mobile computing device, the computer processor being configured by an application to calculate the caloric expenditure by the user for the workout according to one or more fields of the METs table, the user profile and the workout performance history, and based on the workout defined by the application.

In another aspect, a method includes the steps of accessing, by a computer processor, a metabolic equivalent of tasks (METs) table, the METs table comprising a plurality of fields, each representing a physical activity and an associated caloric expenditure for conducting the physical activity. The method further includes selecting, by the computer processor, one or more of the plurality of fields associated with the physical activity that most closely matches the workout, and accessing, by the computer processor from a memory, a user profile and/or a workout performance history for the user and/or other users. The method further includes generating, by the computer processor, a workout for the user according to the user profile and/or the workout performance history. The method further includes calculating, by the computer processor and based on the workout generated for the user, the estimated caloric expenditure by the user for the workout according to the METs table.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

This document describes a system and method employs data mining techniques for estimating METs for specific workouts, related to the workouts in the coaching platform, as described in: U.S. Non-Provisional application Ser. No. 15/017,477, filed Dec. 27, 2011, entitled "FITNESS AND WELLNESS SYSTEM WITH DYNAMICALLY ADJUSTING GUIDANCE"; U.S. Non-Provisional application Ser. No. 13/720,936, filed Dec. 19, 2012, entitled "FITNESS AND WELLNESS SYSTEM WITH DYNAMICALLY ADJUSTING GUIDANCE"; U.S. Non-Provisional application Ser. No. 15/017,537, filed Feb. 5, 2016, entitled "PHYSICAL ACTIVITY COACHING PLATFORM WITH DYNAMICALLY CHANGING WORKOUT CONTENT"; and U.S. Non-Provisional application Ser. No. 14/251,457, filed Apr. 11, 2014, entitled "PHYSICAL ACTIVITY COACHING PLATFORM WITH DYNAMICALLY CHANGING WORKOUT CONTENT", the contents of all of which are incorporated by reference herein for all purposes.

In accordance with a workout builder and coaching platform, each defined workout has a set of instructions/coaching to keep the user on track and following the workout. The coaching platform may have hundreds or thousands of different workouts available for users to perform. Each workout can be generated and tailored specifically for the user's characteristics, skill level, and/or workout or fitness goals. The system and method include assigning METs for the workouts. The METs can be measured and tracked, such as by a user having an HRM or other wearable sensor, so that the METs get more accurate, since calories burned can be more accurately estimated for a specific workout. If a user profile is also known and stored in a database—one or more specific METs can be estimated and assigned for a specific workout based on the user profile.

Figure 1:
FIG. 1 illustrates an exemplary user interface of a system for estimating calorie burn for a run, which lasts 30 minutes.

FIG. 1 illustrates a user interface of a system for estimating calorie burn for a run, which lasts 30 minutes. The user has done a workout with a HRM and follows coaching—gets a 93% score. The user profile: Male 78 kg, burned 395 Cal. Calories=MET_factor×time (h)×weight (kg). MET=Calories/(time×weight). MET_workout_fastfinish1=395/(0.48 h×78 kg)=10.55. By averaging more and more users' profiles, weighted by Workout Scores, an empirical MET value can be calculated for the workout. Next, if a user of 60 kg does the same workout for 30 minutes, without the HRM, their calorie burn can be estimated for the workouts to be: Calories=10.55×0.5×60=316.5 Cals.

Figure 2:
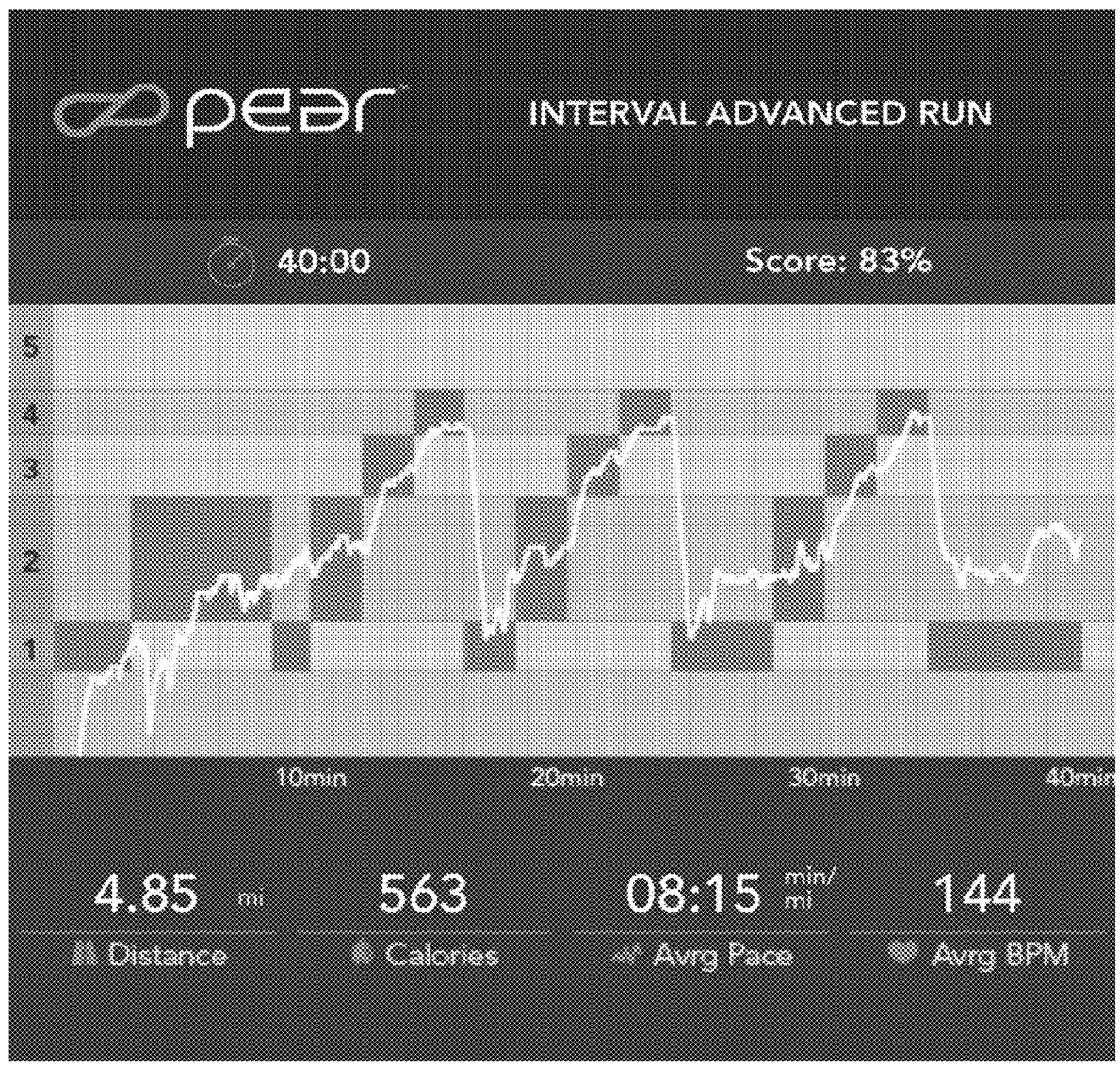
FIG. 2 illustrates an exemplary user interface of a system for estimating calorie burn for an interval advanced run, which lasts 40 minutes.

FIG. 2 illustrates a user interface of a mobile computing device that comprises a system for estimating calorie burn for an interval advanced run, which lasts 40 minutes. The user has done a workout with a HRM and follows coaching—gets an 83% score. The user profile: Male 78 kg, burned 563 Cal. Calories=MET_factor×time (h)×weight (kg). MET=Calories/(time×weight). Accordingly, the MET_workout_intervaladvanced=563/(0.67 h×78 kg)=10.78.

As more people with an HRM or other wearable physiological monitoring device execute the same workout, the MET estimate of the workout can be further improved, such as by averaging the results. The more users that do the workout the more accurate the MET estimate becomes.

The system can calculate more than 1 MET per workout, or calculate an adjustment of the MET based on different factors. For example, different MET's per user profile can be created to further increase accuracy. Or, in another example, the MET can be calculated for male versus female, or for people who weight 130-160 lbs, of people with a certain fitness level (VO2max). The system can also take into account environmental factors such as external temperature, altitude, other weather variables, etc. when users are doing workouts as METs are calculated, and then adjust the MET values based on current altitude or temperature. The system can adjust the empirical workout MET based on fitness level (HRV—stress level, VO2max, Fitness Level). The estimated calorie burn may be different for a more fit and recovered athlete—they have more energy to push and therefore may burn more calories. Further adjustments can include, without limitation: adjusting the empirical MET based on environmental factors (temp, altitude, wind, etc.); adjusting the empirical MET based on galvanic skin response—sweat rate, etc.; and adjusting the empirical MET based on hydration or electrolyte level.

The system can augment estimates based on a wearable device. To further increase the accuracy, the formula can take into account user's movements during the workout to determine how well they are following the coaching. Accordingly, collecting simultaneous accelerometer data of the users, a measure can be built that can assist in the estimation of how well the user is following the workout coaching.

The system can also estimate calorie burn before workout based on user profile and METs. Before a user starts a workout, the system can predict and estimate the calories the user would burn if he/she would do the workout.

In some alternative implementations, Increasing the accuracy of calorie burn can be improved in real-time, by real-time monitoring and sensing by wearables and accelerometers. By using wearables and accelerometers, user movements can be classified and processed in real-time into a MET value, so as to dynamically adjust the calorie burn estimate.

In still yet other implementations, a system as described herein can calculate workout segment based MET values, i.e. generate MET values for one or more subsections of workout. By calculating METs for one or more subsections of a workout, or for each subsection, a coach can construct several different new workouts from workout segments, and still predict Calorie Burn for the user using a Workout Builder system.

Adjustable Meal Plan/Workouts/Coaching

In some implementations, a system integrates weight loss programs and meal plans with the coaching platform. The coaching platform is aware of the user's calorie plan in and calories to be burned. Coaching platform can adjust workout routines based on user's calorie plan or deviations of the meal plan. Coaching and prompts can be associated with meal/weight loss plan related information. "looks like you had a lot of calories yesterday, let's extend this workout with 2 miles to compensate" Or "you are ahead of your calories plan after this workout". Calorie based workouts to be recommended to match the calorie expenditure plan. A calorie based workout advances as the user burns calories. This can be in increments of x cal/sec. Workout will have associated audio prompts set to certain total calorie burn from the start of the workout. Adjusting meal plan based on workout results. Burn off dinner/donut workout. Workout calories burns are tailored to the user's daily plan of burning calories.

Figure 3:
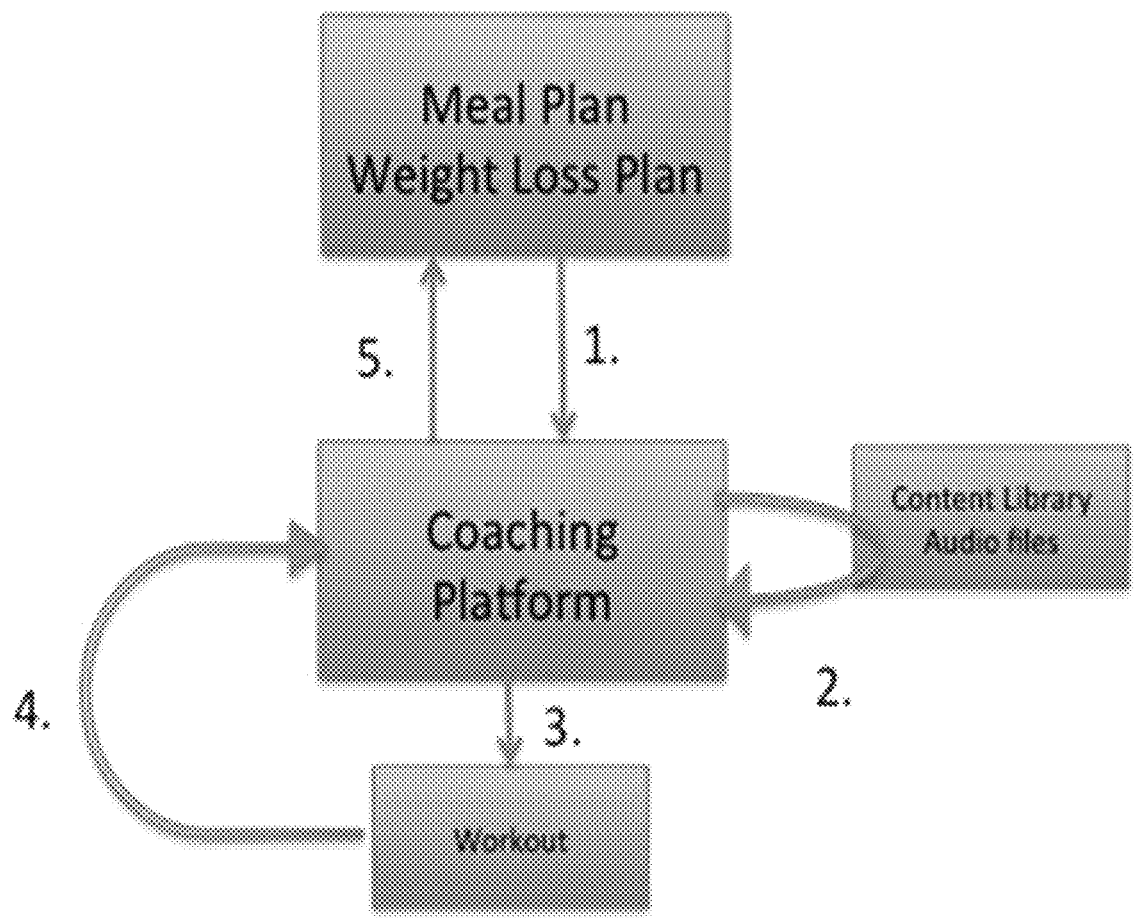
FIG. 3 illustrates a system block diagram and process flow for a system for estimating calorie burn for workouts.

FIG. 3 illustrates a system block diagram and process flow. At 1, a current meal plan status is conveyed to a coaching platform. The user updates the meal plan by updating what he/she has been eating and when. Coaching platform will have an up to date information of the current daily/weekly/monthly calorie balances. At 2, based on desired calories burn amount and situation of the meal-plan, the coaching platform may update a workout with relevant audio coaching for the workout, with playable audio files such as: "well done eating only salad today", or "today's workout is going to be extended by 20 min to account for the extra meal you had in order to keep you on schedule."

At 3, the user is then presented with or recommended a customized workout to be performed next. Workout results, how many calories, what hour zones (fat burn) the user was, etc. are then fed back into the coaching platform (or directly to the Meal Plan), at 5. The coaching platform may suggest appropriate nutrition for the optimal recovery—when to eat after the workout, and what type of and how many carbohydrates or how much protein the user should consume next. The updated results are conveyed to the Meal Plan, where the user may see new adjustments and receive feedback for next meals via the user interface.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:
1. A system comprising:
a memory device storing instructions; and
a processing device operatively coupled to the memory device, the processing device to execute the instructions to perform operations comprising:

accessing a metabolic equivalent of tasks (METs) table, the METs table comprising a plurality of fields associated with a plurality of physical activities, each field of the plurality of fields representing a physical activity and an associated initial caloric expenditure for conducting the physical activity;

identifying a set of factors associated with performance of one or more of the plurality of physical activities by a plurality of users;

generating, based on the set of factors, a first adjusted MET value associated with a first field representing a first physical activity;

accessing, by the processing device from a memory, a user profile and a workout performance history for a user;

generating, by the processing device, a workout for the user according to the user profile and the workout performance history;

receiving, by the processing device from one or more sensors associated with a wearable device associated with the user, biometric data and performance data relating to the user during performance of the workout;

selecting, by the processing device, a subset of the plurality of fields of the METs table associated with one or more physical activities corresponding to the workout, wherein the subset comprises the first adjusted MET value;

calculating, by the processing device and based on the workout generated for the user, the biometric data, the performance data, and one or more corresponding METs values identified from the METs table, an estimated caloric expenditure by the user for the workout; and generating, by the processing device, a graphical user interface comprising a display of the estimated caloric expenditure by the user for the workout.

2. The system of claim 1, wherein the workout performance history comprises caloric burn data of past workouts.

3. The system of claim 1, further comprising one or more wearable sensors operatively coupled to the processing device and configured to be worn by the user, each of the one or more wearable sensors sensing biometric data about the user during the workout.

4. The system of claim 1, wherein the one or more sensors comprises an accelerometer, and wherein the biometric data comprises data representing movement of the user during the workout.

5. The system of claim 1, wherein the user profile comprises a weight of the user.

6. The system of claim 1, wherein the user profile comprises one or more workout goals inputted by the user, and wherein the one or more workout goals comprise a caloric expenditure goal.

7. A method comprising:
accessing, by a computer processor, a metabolic equivalent of tasks (METs) table, the METs table comprising a plurality of fields associated with a plurality of physical activities, each field of the plurality of fields representing a physical activity and an associated initial caloric expenditure for conducting the physical activity;

identifying a set of factors associated with performance of one or more of the plurality of physical activities by a plurality of users;

generating, based on the set of factors, a first adjusted MET value associated with a first field representing a first physical activity;

accessing, by the computer processor from a memory, a user profile and a workout performance history for a user;

generating, by the computer processor, a workout for the user according to the user profile and the workout performance history;

receiving, by the computer processor from one or more sensors associated with a wearable device associated with the user, biometric data and performance data relating to the user during performance of the workout;

selecting, by the computer processor, a subset of the plurality of fields of the METs table associated with one or more physical activities corresponding to the workout, wherein the subset comprises the first adjusted MET value;

calculating, by the computer processor and based on the workout generated for the user, the biometric data, the performance data, and one or more corresponding METs values identified from the METs table, an estimated caloric expenditure by the user for the workout; and generating a graphical user interface comprising a display of the estimated caloric expenditure by the user for the workout.

8. The method of claim 7, further comprising receiving, by the computer processor from one or more sensors, biometric data and performance data for the user during the workout.

9. The method of claim 8, wherein the one or more sensors comprises an accelerometer, and wherein the biometric data and performance data comprises data representing a movement of the user during the workout.

10. The method of claim 9, further comprising adjusting, by the computer processor, the estimated caloric expenditure by the user for the workout based at least in part on one or more of the biometric data or the performance data.

11. The method of claim 7, wherein the user profile comprises a historical performance record of the user for one or more past workouts.

12. The method of claim 7, wherein the user profile comprises a set of workout goals associated with the user.

* * * * *